United States Patent
Li et al.

(10) Patent No.: US 12,128,139 B2
(45) Date of Patent: Oct. 29, 2024

(54) HYDRATION GEL PARTICLE FOR CHEMOEMBOLIZATION COMPRISING BIODEGRADABLE POLYMER

(71) Applicant: NEXTBIOMEDICAL CO., LTD., Incheon (KR)

(72) Inventors: Yi Xian Li, Incheon (KR); Choong Ryeol Choi, Incheon (KR)

(73) Assignee: NEXTBIOMEDICAL CO., LTD., Incheon (KR)

(*) Notice: Subject to any disclaimer, the term of this patent is extended or adjusted under 35 U.S.C. 154(b) by 662 days.

(21) Appl. No.: 17/297,254

(22) PCT Filed: Nov. 29, 2019

(86) PCT No.: PCT/KR2019/016792
§ 371 (c)(1),
(2) Date: May 26, 2021

(87) PCT Pub. No.: WO2020/111895
PCT Pub. Date: Jun. 4, 2020

(65) Prior Publication Data
US 2022/0023218 A1   Jan. 27, 2022

(30) Foreign Application Priority Data

Nov. 30, 2018  (KR) .................. 10-2018-0153064

(51) Int. Cl.
*A61K 9/16* (2006.01)
*A61B 17/12* (2006.01)
*A61K 31/4745* (2006.01)

(52) U.S. Cl.
CPC .......... *A61K 9/1652* (2013.01); *A61K 9/1658* (2013.01); *A61K 9/1682* (2013.01);
(Continued)

(58) Field of Classification Search
CPC .. A61K 9/1652; A61K 9/1658; A61K 9/1682; A61K 31/4745; A61K 31/704;
(Continued)

(56) References Cited

U.S. PATENT DOCUMENTS 5,629,191 A * 5/1997 Cahn .................. C12N 5/0075
                                                   435/395
2006/0067883 A1* 3/2006 Krom .................... A61P 19/02
                                                    424/1.29
(Continued)

FOREIGN PATENT DOCUMENTS

CN         102397593 A     4/2012
CN         102429858 A     5/2012
(Continued)

OTHER PUBLICATIONS

Makadia HK, Siegel SJ. Poly Lactic-co-Glycolic Acid (PLGA) as Biodegradable Controlled Drug Delivery Carrier. Polymers (Basel). Sep. 1, 2011;3(3):1377-1397. doi: 10.3390/polym3031377. Epub Aug. 26, 2011. PMID: 22577513; PMCID: PMC3347861. (Year: 2011).*

(Continued)

*Primary Examiner* — Isaac Shomer
*Assistant Examiner* — Bryan James Rego
(74) *Attorney, Agent, or Firm* — Harness, Dickey & Pierce, P.L.C.

(57) ABSTRACT

The present invention relates to microparticles that can be used as drug-loaded hydrogel particles for embolization and a method for manufacturing same. The microparticles of the present invention have a very excellent anticancer agent adsorption ability, a short anticancer agent adsorption time, and a controllable decomposition time when administered in vivo. Therefore, when the microparticles of the present invention are used in chemoembolization, not only the (Continued)

anticancer effect is excellent, but also side effects can be minimized.

6 Claims, 6 Drawing Sheets

(52) U.S. Cl.
CPC .... *A61K 31/4745* (2013.01); *A61B 17/12186* (2013.01); *A61B 17/12195* (2013.01)

(58) Field of Classification Search
CPC ........ A61B 17/12186; A61B 17/12195; A61L 2300/416; A61L 2430/36; A61L 24/0015; A61L 24/0042; A61L 24/043; A61L 24/102; A61L 24/104; A61P 35/00
See application file for complete search history.

(56) References Cited

U.S. PATENT DOCUMENTS

| | | | |
|---|---|---|---|
| 2007/0031468 | A1 | 2/2007 | Abrahams et al. |
| 2012/0276151 | A1* | 11/2012 | Lewis ................ A61K 9/1635 |
| | | | 977/788 |
| 2014/0274945 | A1 | 9/2014 | Blaskovich et al. |

FOREIGN PATENT DOCUMENTS

| | | | |
|---|---|---|---|
| CN | 102911380 | A | 2/2013 |
| CN | 103550834 | A | 2/2014 |
| CN | 103990185 | A | 8/2014 |
| JP | 2001-039869 | A | 2/2001 |
| JP | 2005-112858 | A | 4/2005 |
| JP | 2010-162063 | A | 7/2010 |
| JP | 2013-540723 | A | 11/2013 |
| JP | 5792691 | B2 | 10/2015 |
| KR | 10-2014-0031463 | A | 3/2014 |
| KR | 10-1569482 | B1 | 11/2015 |
| KR | 20170093400 | A * | 8/2017 |
| TW | 201444587 | A | 12/2014 |

OTHER PUBLICATIONS

Weng, Lihui et al. "In vitro and in vivo suppression of cellular activity by guanidinoethyl disulfide released from hydrogel microspheres composed of partially oxidized hyaluronan and gelatin." Biomaterials vol. 29,31 (2008): 4149-56. doi: 10.1016/j.biomaterials.2008. 07.026 (Year: 2008).*

Esposito, Elisabetta, Rita Cortesi, and Claudio Nastruzzi. "Gelatin microspheres: influence of preparation parameters and thermal treatment on chemico-physical and biopharmaceutical properties." Biomaterials 17.20 (1996): 2009-2020 (Year: 1996).*

Komlev, Vladimir S., Serguei M. Barinov, and Elena V. Koplik. "A method to fabricate porous spherical hydroxyapatite granules intended for time-controlled drug release." Biomaterials 23.16 (2002): 3449-3454 (Year: 2002).*

"Yang Su Geun, KR 20170093400 A, Feb. 5, 2016, machine translation" (Year: 2017).*

Office Action from corresponding Korean Patent Application No. 10-2019-0157703, issued Jan. 27, 2022.

Brown, K. E., et al.; "Gelatin/Chondroitin 6-SULFATE Microspheres for the Delivery of Therapeutic Proteins to the Joint", Arthritis & Rheumatism, vol. 41, No. 12. Dec. 1998, pp. 2185-2195.

Dawlee, S., et al.; "Oxidized Chondroitin Sulfate-Cross-Linked Gelatin Matrixes: A New Class of Hydrogels", Biomacromolecules 2005, 6, 2040-2048.

Extended European Search Report from corresponding European Patent Application No. 19891265.1, dated Dec. 20, 2021.

Lai, J., et al.; "Ocular biocompatibility of gelatin microcarriers functionalized with oxidized hyaluronic acid", Materials Science and Engineering C 72, 2017, pp. 150-159.

Truong, V. L., et al.; "Targeted Delivery of Immunomicrospheres", Drug Delivery, 2, 166-174, 1995.

Office Action from corresponding Chinese Patent Application No. 201980079960.2, dated Jan. 26, 2022.

Yi, W., et al.; "Preparation and Biological Characteristics of a New Doxorubicin-gelatin-microspheres for Hepatic Artery Embolization", J Sichuan Univ (Med Sci Edi), 2011, 42(1), 119-124.

Office Action from corresponding Korean Patent Application No. 10-2019-0157703, issued on Jun. 14, 2021.

Weng, L., et al.; "In vitro and in vivo suppression of cellular activity by guanidinoethyl disulfide released from hydrogel microspheres composed of partially oxidized hyaluronan and gelatin", Biomaterials 29 (2008) 4149-4156.

International Search Report from corresponding PCT Application No. PCT/KR2019/016792, dated Mar. 27, 2020.

Written Decision on Registration of KR 10-2019-0157703, issued on Jul. 28, 2022.

* cited by examiner

HYDRATION GEL PARTICLE FOR CHEMOEMBOLIZATION COMPRISING BIODEGRADABLE POLYMER

CROSS-REFERENCE TO RELATED APPLICATIONS

This application is a national phase application of PCT Application No. PCT/KR2019/016792 filed on Nov. 29, 2019, which claims the benefit of and priority to Korean Patent Application No. 10-2018-0153064 filed on Nov. 30, 2018. The entire disclosures of the applications identified in this paragraph are incorporated herein by references.

TECHNICAL FIELD

The present disclosure relates to hydrogel particles for chemoembolization, the hydrogel particles containing a biodegradable polymer and having a spherical shape.

BACKGROUND ART

The rapid development of diagnostic imaging technology enables the pinpointing of cancer sites and blood vessels supplying blood to cancer and the conduction of cancer therapy through various manners, such as irradiation, surgical removal, and tumor necrosis using vascular embolism. Out of these, embolotherapy is a type of treatment in which the blood supply to a tumor is blocked by infarction of a specific blood vessel supplying blood to the tumor through carotid access of a catheter, thereby inducing the necrosis of the tumor. Recently, transcatheter arterial chemoembolization (TACE) is the most commonly used method for treatment of hepatocellular carcinoma. TACE is a treatment that simultaneously pursues an embolization effect on the arteries supplying blood flow to tumors and an anticancer effect through carotid artery injection of anticancer drugs. Normal livers receive 70-80% of the blood flow and 50% of the required oxygen volume from portal veins, whereas liver cancer cells mostly receive the same from hepatic arteries. Therefore, TACE can be used to treat tumors comparatively selectively since the embolization of hepatic arteries causes more severe damage to liver cancer cells than normal hepatocytes.

In the early days of the TACE procedure, gelatin sponge particles were soaked with an anticancer agent and administered. After it was discovered that Lipiodol enters liver cancer tissues with a much higher proportion than normal liver tissues and can remain in place for up to several months in the host, Lipiodol started to be administered while being mixed with anticancer drugs. Lipiodol TACE is a method in which a suspension is first prepared by mixing Lipiodol and an anticancer drug, and injected into the artery of a tumor, and then gelatin sponge particles are additionally injected to embolize the artery, thereby minimizing the loss of the anticancer drug. The advantage of Lipiodol TACE is that the exposure to a high-concentration anticancer drug for a certain period of time increases a therapeutic effect including tumor necrosis. However, Lipiodol TACE has disadvantages in that the damage to normal liver tissue as well as the damage to tumor tissue is increased, and an anticancer drug spreads throughout the body as well as the liver cancer tissue, causing unpredicted side effects. Therefore, a measure to maximize an anticancer effect while preserving normal liver tissues has begun to attract attention, and a drug-loaded embolic agent has been developed that can continuously release a predetermined concentration of drug instead of the release of a high-concentration drug at once. The drug-loaded embolic agent, which is a bead-shaped embolic agent, has a uniform particle size, and completely adsorb a drug if left in mix with a drug for 1 hour immediately before use. When the hepatic artery is embolized with the drug-adsorbed embolic agent, the anticancer drug is slowly released over about 14 days. While conventional chemoembolization (TACE) requires hospitalization for an average of 8.5 days, the chemoembolization using a drug-loaded embolic agent has been reported to cause no problems even in a case of hospitalization for only one day due to a significant decrease in side effects. Chemoembolization using a drug-loaded embolic agent is currently the most widely used method for treating liver cancer, and in recent years, such chemoembolization is used more and more for the treatment of various indications, such as uterinemyoma, prostate cancer, lung cancer, and kidney cancer. Representative products of drug-loaded embolic agents are known to be Cali-gel™, HepaSphere™, DC Bead™, and the like.

Embolic agents that have been currently used in hepatic arterial chemoembolization are classified into two types: general embolic agents and drug-loaded embolic agents. General embolic agents may be divided into degradable and non-degradable embolic agents, and only non-degradable embolic agents are available for drug loading. According to studies, the permanent embolization of the blood vessels of a tumor precludes the possibility of re-operation of original blood vessels, and angiogenesis occurs in the tumor, and thus the treatment is difficult. Therefore, the commercially available Cali-gel™ is a typical biodegradable embolic agent, but is known to be degraded in the body within one week, resulting in the re-opening of blood vessels, and thus definite necrosis of the tumor cannot be induced. On the other hand, HepaSphere™ or DC Bead™ have an advantage of drug loading, but these are non-degradable, and thus re-operation is impossible, and it has been reported that new blood vessels are formed in tumors after the completion of the procedure.

Therefore, the present inventors have conducted efforts to develop an embolic agent, which allows drug loading while having an appropriate time of degradation required for treatment.

SUMMARY

Technical Problem

The present inventors have conducted efforts to develop an embolic agent that enables allowing drug loading while having an appropriate time of degradation required for treatment. As a result, the present inventors established that microparticles prepared using gelatin and/or collagen and an oxidized anionic polymer can be used as hydrogel particles for embolization, which have superb drug adsorption ability and release ability and of which the time of degradation in vivo is controllable.

Accordingly, a purpose of the present disclosure is to provide microparticles containing: (a) gelatin, collagen, or a mixture thereof; and (b) a biodegradable anionic polymer, and to provide a manufacturing method therefor.

Technical Solution

In accordance with an aspect of the present disclosure, the present invention provides microparticles containing: (a) gelatin, collagen, or a mixture thereof; and (b) a biodegradable anionic polymer.

In an embodiment of the present disclosure, the biodegradable anionic polymer is an oxidized anionic polymer.

As used herein, the term "biodegradable" refers to being degradable when exposed to a physiological solution, and for example, refers to being degradable by, for example, PBS, physiological saline, distilled water, in vivo bodily fluids of mammals including a human being, or microorganisms.

In a specific embodiment of the present disclosure, the biodegradable anionic polymer is selected from the group consisting of chondroitin sulfate, dextran sulfate, dermatan sulfate, sodium alginate sulfate, heparin, keratan sulfate, hyaluronic acid, or a mixture thereof.

In a more specific embodiment of the present disclosure, the biodegradable anionic polymer is selected from the group consisting of oxidized chondroitin sulfate, oxidized dextran sulfate, oxidized dermatan sulfate, oxidized sodium alginate sulfate, oxidized heparin, oxidized keratan sulfate, oxidized hyaluronic acid, or a mixture thereof.

In an embodiment of the present disclosure, the oxidized chondroitin sulfate, oxidized dextran sulfate, oxidized dermatan sulfate, oxidized sodium alginate sulfate, oxidized heparin, oxidized keratan sulfate, and oxidized hyaluronic acid may be prepared by reaction of chondroitin sulfate, dextran sulfate, dermatan sulfate, sodium alginate sulfate, heparin, keratan sulfate, and hyaluronic acid with sodium periodate for 6 to 24 hours, 8 to 24 hours, 10 to 24 hours, 12 to 24 hours, 18 to 24 hours, more specifically, 12 hours, 14 hours, 16 hours, 18 hours, 20 hours, 22 hours, or 24 hours, but are not limited thereto.

In a specific embodiment of the present disclosure, in a case where the biodegradable anionic polymer of the present disclosure is chondroitin sulfate, the degree of substitution may be controlled by the weight percent of sodium periodate reacting with chondroitin sulfate. For example, the degree of substitution of chondroitin sulfate may be controlled to be 75-85% by reaction of 15 g of sodium periodate and 50 g of chondroitin sulfate at room temperature for 18 hours; the degree of substitution of chondroitin sulfate may be controlled to be 55-60% by reaction of 12 g of sodium periodate at room temperature for 18 hours; the degree of substitution of chondroitin sulfate may be controlled to be 30-55% by reaction of 6 g of sodium periodate at room temperature for 18 hours; the degree of substitution of chondroitin sulfate may be controlled to be 25-30% by reaction of 5.5 g of sodium periodate at room temperature for 18 hours; the degree of substitution of chondroitin sulfate may be controlled to be 20-25% by reaction of 5 g of sodium periodate at room temperature for 18 hours; and the degree of substitution of chondroitin sulfate may be controlled to be 16-20% by reaction of 4.5 g of sodium periodate at room temperature for 18 hours.

In an embodiment of the present disclosure, the weight ratio of (a) the gelatin, collagen, and the mixture thereof, and (b) the biodegradable anionic polymer, constituting the microparticles of the present disclosure, may be 5:1 to 1:5, 3:1 to 1:3, or 2:1 to 1:2, and specifically, 1:1 to 1:5, 1:1 to 1:4, 1:1 to 1:3, 1:1 to 1:2, 5:1 to 1:1, 4:1 to 1:1, 3:1 to 1:1, 2:1 to 1:1, 1:1, 1:1.5, 1:2, 1:3, 1:4, 1:5, 1.5:1, 2:1, 3:1, 4:1, 5:1, 1.5:2, 3:2, 5:2, 2:3, 4:3, 5:3, 3:4, 5:4, 2:5, 3:5, 4:5, 5:1, 4:1, 3:1, 2:1, or 1.5:1, but is not limited thereto.

In an embodiment of the present disclosure, the time required for degrading the microparticles of the present disclosure increases as the content of gelatin constituting the microparticles increases.

In an embodiment of the present disclosure, when the microparticles containing gelatin and oxidized chondroitin sulfate of the present disclosure are swollen in 1×PBS and then the time taken for the microparticles to completely degrade with shaking at 100 rpm in a shaking water bath is measured, the time of degradation is 5 to 15 days or 5 to 10 days when the weight ratio of gelatin to chondroitin sulfate is 3 to 7.5; the time of degradation is 15 to 25 days when the weight ratio of gelatin to chondroitin sulfate is 5 to 7.5; and the time of degradation is 25 to 35 days when the weight ratio of gelatin to chondroitin sulfate is 5 to 7.5.

In an embodiment of the present disclosure, the time required for degrading the microparticles of the present disclosure increases as the content of chondroitin sulfate constituting the microparticles increases.

In an embodiment of the present disclosure, when the microparticles containing gelatin and oxidized chondroitin sulfate of the present disclosure are swollen in 1×PBS, and then the time taken for the microparticles to completely degrade with shaking at 100 rpm in a shaking water bath is measured, the time of degradation is 3 to 5 days when the weight ratio of chondroitin sulfate to gelatin is 3-6 to 3; the time of degradation is 5 to 10 days when the weight ratio of chondroitin sulfate to gelatin is 6-8 to 3; and the time of degradation is 10 to 15 days when the weight ratio of chondroitin sulfate to gelatin is 8-12 to 3.

In an exemplary embodiment of the present disclosure, the microparticles of the present disclosure exhibit the highest drug adsorption ability when the weight ratio of gelatin and oxidized chondroitin sulfate constituting the microparticles of the present disclosure is 1:1.5, that is, 2:3.

In an embodiment of the present disclosure, the time required for degrading the microparticles of the present disclosure is increased as the degree of substitution of chondroitin sulfate constituting the microparticles increases.

In an embodiment of the present disclosure, when the microparticles containing gelatin and oxidized chondroitin sulfate of the present disclosure are swollen in 1×PBS and the time taken for the microparticles to completely degrade with shaking at 100 rpm in a shaking water bath is measured, the time of degradation is about 25 to 35 days when the degree of substitution of chondroitin sulfate is 50-70%; the time of degradation is about 10 to 20 days when the degree of substitution of chondroitin sulfate is 30-50%; and the time of degradation is about 4 to 10 days when the degree of substitution of chondroitin sulfate is 10-30%.

In another embodiment of the present disclosure, the microparticles of the present disclosure may be used for chemoembolization. More specifically, the microparticles of the present disclosure may be used for transcatheter arterial chemoembolization (TACE). Therefore, the microparticles are characterized by having a drug adsorption ability.

In an embodiment of the present disclosure, the drug adsorbed to the microparticles of the present disclosure is an anticancer drug. The anticancer drug may be an anthracycline-based anticancer drug or irinotecan.

In a specific embodiment of the present disclosure, the anthracycline-based anticancer drug is selected from the group consisting of daunorubicin, doxorubicin, epirubicin, idarubicin, gemcitabine, mitoxantrone, pirarubicin, and valrubicin, but is not limited thereto.

The microparticles of the present disclosure are characterized by microspheres having a spherical shape and a micro-unit diameter.

As used herein, the term "microparticles" is expressed by microspheres, hydrogel particles, microspheres, or fine particles.

The anticancer drug adsorption ability of the drug-loaded hydrogel particles for embolization according to an embodiment of the present disclosure shows an adsorption time of 5 to 20 minutes per 2 ml of hydrogel. This indicates a 3- to 12-fold improvement compared with the currently available products, such as HepaSphere™ or DC Bead™.

In accordance with another aspect of the present disclosure, the present invention provides a method for manufacturing microparticles, the method comprising:

(a) dissolving gelatin, collagen, or a mixture thereof in an aqueous solvent;

(b) dissolving a biodegradable anionic polymer in an aqueous solvent; and (c) mixing the solution of gelatin, collagen, or a mixture thereof and the biodegradable anionic polymer solution.

In an embodiment of the present disclosure, the biodegradable anionic polymer is an oxidized anionic polymer.

In a specific embodiment of the present disclosure, the biodegradable anionic polymer is selected from the group consisting of chondroitin sulfate, dextran sulfate, dermatan sulfate, sodium alginate sulfate, heparin, keratan sulfate, hyaluronic acid, or a mixture thereof.

In a more specific embodiment of the present disclosure, the biodegradable anionic polymer is selected from the group consisting of oxidized chondroitin sulfate, oxidized dextran sulfate, oxidized dermatan sulfate, oxidized sodium alginate sulfate, oxidized heparin, oxidized keratan sulfate, oxidized hyaluronic acid, or a mixture thereof.

In an embodiment of the present disclosure, the aqueous solvents for dissolving the gelatin, collagen, or mixture thereof, and the biodegradable anionic polymer therein include distilled water, physiological saline, PBS, and the like, and encompass, without limitation, non-toxic solvents that causes no stability and toxicity problems even when administered in vivo, and the term has only a passive meaning to distinguish the same from an organic solvent, and is not limited to the aqueous solvents exemplified above.

In an embodiment of the present disclosure, the manufacturing method of the present disclosure further comprises (d) adding the mixture solution as the resultant product in step (c) to an organic solvent, followed by emulsification. The organic solvent is n-butyl acetate, cellulose acetate butyrate, medium chain triglyceride (MCT) oil, or a mixture solvent thereof. Compared with the use of n-butyl acetate or cellulose acetate butyrate as an organic solvent, the use of the MCT oil results in a non-uniform diameter of the manufactured microparticles and the clumping thereof. Therefore, the organic solvent is preferably n-butyl acetate or cellulose acetate butyrate.

In a further embodiment of the present disclosure, the manufacturing method of the present disclosure further comprises (e) washing and drying the microparticles generated by the emulsification performed in step (c).

The washing is conducted with an organic solvent selected from n-butyl acetate, cellulose acetate butyrate, medium chain triglyceride (MCT) oil, or a mixture solvent thereof, but the same type of organic solvent as used in the emulsification in step (c) is preferably used.

In a further embodiment of the present disclosure, the manufacturing method of the present disclosure further comprises (f) subjecting the microparticles generated by the emulsification to thermal treatment at a temperature of 90 to 200° C. for 0.5 to 5 hours. The temperature for thermal treatment is specifically 100 to 150° C., 120 to 150° C., 130 to 150° C., 140 to 150° C., 100 to 200° C., 120 to 200° C., 130 to 200° C., 140 to 200° C., 150 to 200° C., 150 to 180° C., 150 to 160° C., or 150° C., and the time of thermal treatment is specifically 1 to 10 hours, 2 to 10 hours, 3 to 10 hours, 5 to 10 hours, 1 to 7 hours, 2 to 7 hours, 3 to 7 hours, 5 to 7 hours, 1 to 5 hours, 2 to 5 hours, 3 to 5 hours, 1 to 4 hours, 2 to 4 hours, 3 to 4 hours, 1 to 3 hours, 2 to 3 hours, 1 hour, 2 hours, 3 hours, 4 hours, or 5 hours, but is not limited thereto.

In a specific embodiment of the present disclosure, the time required for the degradation of microparticles increases as the thermal treatment time increases.

In an exemplary embodiment of the present disclosure, when the microparticles of the present disclosure are thermally treated for 2 hours or less, the microparticles are degraded in 1×PBS within 7 days, but when thermally treated for 2 hours or more, for example 5 hours, the time of degradation in 1×PBS can be extended to about 30 days.

In the thermal treatment in the present disclosure, any means that can apply a heat with a preferable temperature may be used without limitation, for example, an electric oven, a gas oven, microwave oven, heating in an aqueous solvent or an organic solvent, and the like.

In an embodiment of the present disclosure, the microparticles prepared by the manufacturing method comprising the thermal treatment step of the present disclosure have a much superior drug adsorption ability compared with microparticles that are not thermally treated.

In a further embodiment of the present disclosure, the manufacturing method of the present disclosure further comprises (g) washing (or hydrating) the thermally treated microparticles.

Furthermore, the manufacturing method of the present disclosure further comprises (h) dehydrating and drying the microparticles. The washing (or hydrating) and dehydrating steps enable the removal of byproducts generated from the thermal treatment process to prevent the generation of floaters at the time of drug adsorption and enables the increase in drug adsorption ability.

The manufacturing method of the present disclosure may further comprises classifying the manufactured microparticles according to size (diameter) through sieving. The size (diameter) of the microparticles may be classified into sizes of, for examples, 75-150 μm, 100-300 μm, 300-500 μm, 500-700 μm, or 700-900 μm, but it would be obvious to a person skilled in the art that the sizes of the microparticles to be classified are not limited thereto.

Since the manufacturing method according to an aspect of the present disclosure is a method for manufacturing the foregoing microparticles according to an aspect of the present disclosure, the description of the category common to the foregoing microparticles is equally applied to the manufacturing method of the present disclosure.

Advantageous Effects

The present disclosure provides microparticles usable as drug-loaded hydrogel particles for embolization and a manufacturing method therefor.

(1) The time for biodegrading the microparticles provided in the present disclosure can be controlled to be 1-12 weeks or more.

(2) The microparticles provided in the present disclosure require 5 to 20 minutes for drug loading, and thus exhibit a significantly improved anticancer drug adsorption rate.

(3) The embolic agent provided in the present disclosure is degraded for a short time, and thus reduces the formation of angiogenesis that may be caused by a non-degradable embolic agent.

(4) The embolic agent provided in the present disclosure is composed of only a biocompatible polymer without any chemical crosslinker or additive, and thus is very safe.

DETAILED DESCRIPTION

Hereinafter, the present disclosure will be described in more detail with reference to examples. These examples are provided only for the purpose of illustrating the present disclosure in more detail, and therefore, according to the purpose of the present disclosure, it would be apparent to a person skill in the art that these examples are not construed to limit the scope of the present disclosure.

EXAMPLES

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Example 1

Oxidation Reaction of Chondroitin Sulfate

First, 50 g of chondroitin sulfate was completely dissolved in 450 ml of distilled water. Then, 5 g of sodium periodate was completely dissolved in 50 ml of distilled water, and this solution was added to 450 ml of the chondroitin sulfate solution, followed by stirring at room temperature for 18 hours. After the reaction was completed, the residual sodium periodate was removed by ultra-filtration, and oxidized chondroitin sulfate having a degree of substitution (DS) of about 25% was obtained by vacuum drying. The results of the degree of substitution according to the ratio of chondroitin sulfate and sodium periodate added are shown in Table 1 below.

TABLE 1

| Chondroitin Sulfate | Sodium Periodate | Distilled water | Reaction time | Degree of substitution (DS) |
|---|---|---|---|---|
| 50 g | 15 g | 500 ml | 18 hours | 75-80% |
|  | 12 g |  |  | 55-60% |
|  | 6 g |  |  | 30-35% |
|  | 5.5 g |  |  | 25-30% |
|  | 5 g |  |  | 20-25% |
|  | 4.5 g |  |  | 16-20% |

Example 2

Composition Ratio of Drug-Loaded Hydrogel Particles for Embolization

To manufacture drug-loaded hydrogel particles for embolization of the present disclosure, the composition proportions of gelatin and the anionic polymer oxidized chondroitin sulfate and the degree of substitution of the oxidized chondroitin sulfate are shown in Table 2 below. A hydrogel stock solution was prepared by mixing a gelatin aqueous solution and an oxidized chondroitin sulfate aqueous solution, and the contents of gelatin and oxidized chondroitin sulfate in Table 2 represent the contents of the two substances in the hydrogel stock solution prepared by mixing the two aqueous solutions.

TABLE 2

| Composition | Gelatin (%) | Oxidized chondroitin sulfate (%) | |
|---|---|---|---|
| 1 | 3 | 7.5% | DS of about 59% |
| 2 | 4 | | |
| 3 | 5 | | |
| 4 | 5 | 5% | DS of about 41% |
| 5 | | 7.5% | |
| 6 | 5 | 5% | DS of about 32% |
| 7 | | 7.5% | |
| 8 | | 10% | |
| 9 | 5 | 7.5% | DS of about 20% |
| 0 | | 10 | |

* The percent (%) indicating the content of each ingredient in the hydrogel stock solution Example 3

Manufacture of Drug-Loaded Hydrogel Particles for Embolization 1 (Thermal Treatment)

Figure 1:
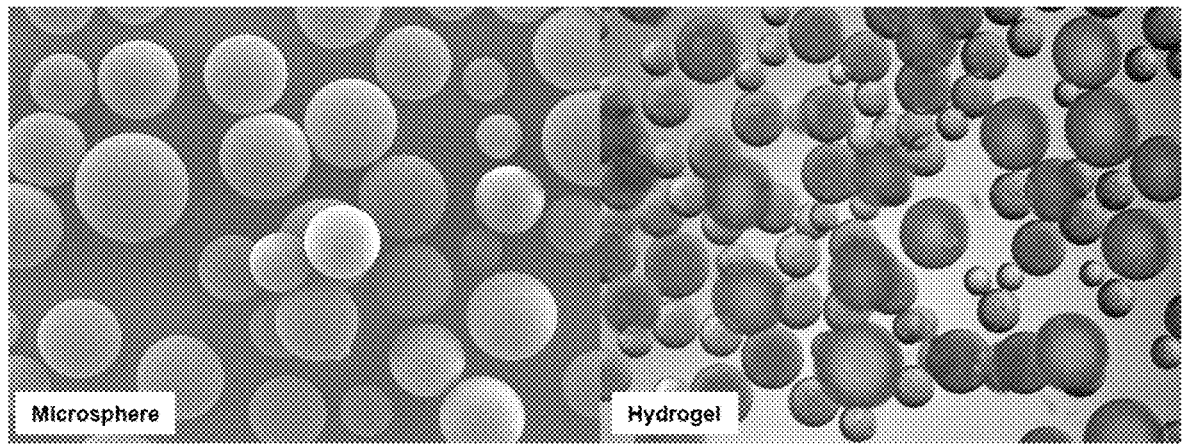
FIG. 1 shows images of powdered microspheres and hydrogel particles manufactured through thermal treatment of the present disclosure.

First, 60 ml of a gelatin solution and 60 ml of an oxidized chondroitin sulfate solution were mixed in a tube according to each composition shown in Table 2 above, and the tube was immersed in a water bath at 50° C., followed by stirring for 10 minutes. Then, 120 ml of the mixture solution of the gelatin solution and the oxidized chondroitin sulfate solution was sprayed into 600 ml of a collection solution (medium chain triglyceride oil (MCT oil)); or n-butyl acetate (containing 10% cellulose acetate butyrate)), maintained at 4° C., by using an encapsulator, while the collection solution was stirred, thereby preparing an emulsion (microparticles). After the spraying of the mixture solution was completed, the stirring was stopped, the particles formed in the collection solution were settled by a long period of stabilization, and the collection solution in the upper layer was discarded. Washing was sequentially conducted using n-butyl acetate and acetone, and vacuum drying was performed, thereby obtaining microspheres (microparticles). The obtained microspheres were thermally treated at 150° C. for 2 hours, and immersed in distilled water until completely swollen or hydrated, and then hydrogel particles with a diameter of 100-300 μm were collected through sieving. The collected hydrogel particles were dehydrated with acetone, followed by vacuum drying, thereby obtaining final powdered microspheres. Images of the manufactured final powdered microspheres and the hydrogel particles upon swelling are shown in FIG. 1.

Example 4

Drug Adsorption Test of Drug-Loaded Hydrogel Particles for Embolization

Figure 2A:
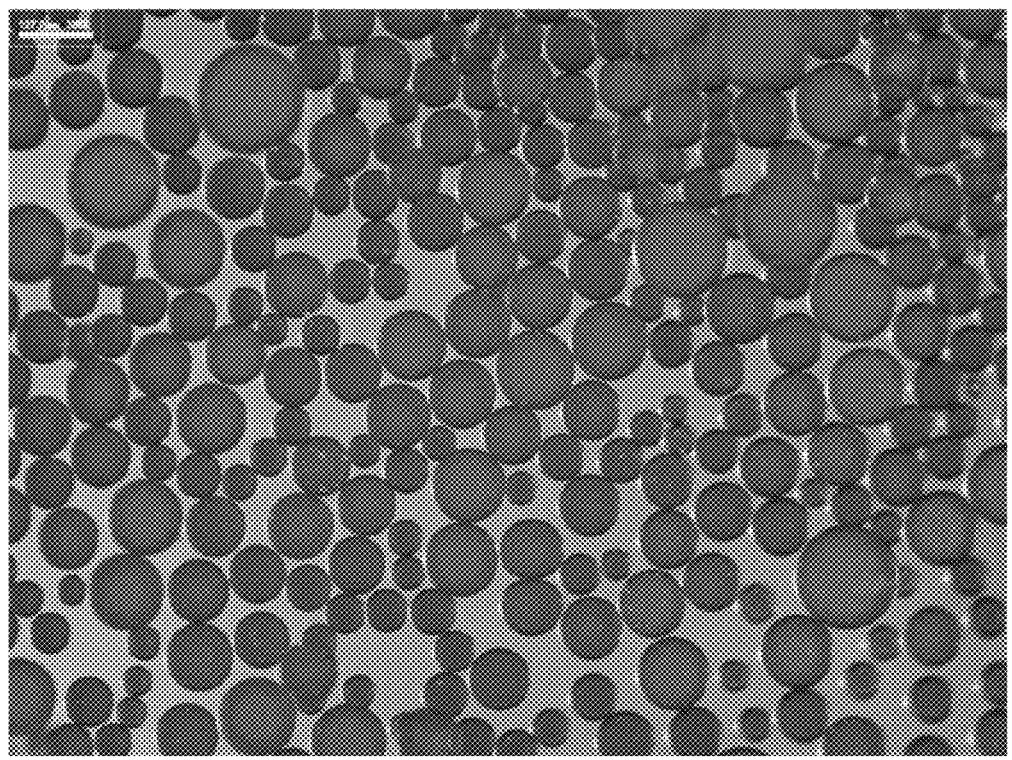
FIG. 2A shows an enlarged image of observation of doxorubicin-adsorbed hydrogel particles of the present disclosure.
Figure 2B:
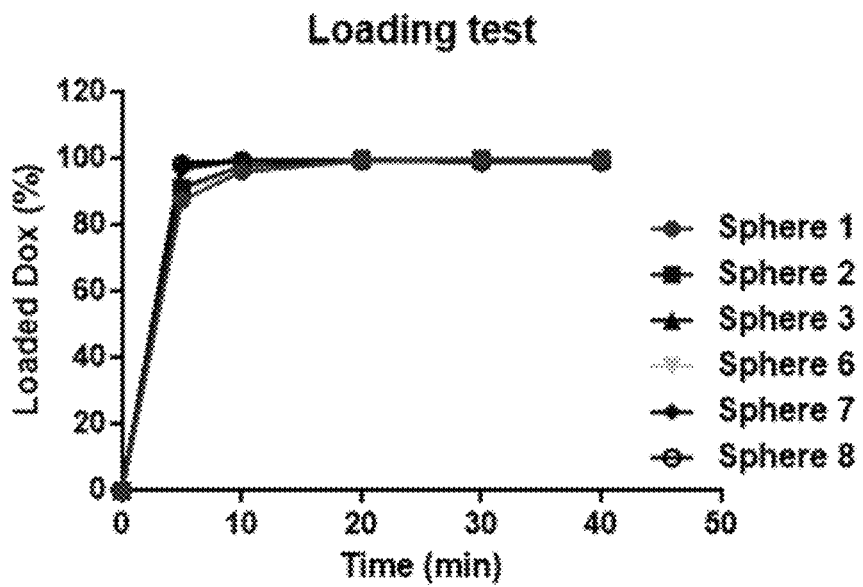
FIG. 2B illustrates the doxorubicin adsorption ability of hydrogel particles of the present disclosure over time.

A doxorubicin adsorption test was conducted on the microspheres manufactured according to each of the compositions in Example 2 by the method in Example 3. First, a 5 mg/ml solution of doxorubicin was prepared by dissolving 50 mg of doxorubicin in 10 ml of distilled water. Then, about 270-300 mg of the manufactured microspheres were collected in a 10 ml-glass vial, and 10 ml of the prepared 5 mg/ml doxorubicin solution was slowly added thereto. Shaking was conducted three to five times once every two minutes so that the microspheres were well mixed with doxorubicin. After 5, 10, and 20 minutes, the content of doxorubicin contained in the supernatant was measured to check the amount of the drug adsorbed to the microspheres. The total volume of the drug-adsorbed hydrogel particles was about 2 ml. The image of the drug-adsorbed hydrogel particles is shown in FIG. 2A, and the test results are shown in Table 3 and FIG. 2b. As can be seen from the microsphere weights in Table 3, the degree of swelling of microspheres after drug adsorption varied depending on the degree of substitution of chondroitin sulfate. Specifically, the volume after hydrogenation became larger as the degree of substitution of chondroitin sulfate was lower.

TABLE 3

| Composition | Gelatin (%) | Oxidized chondroitin sulfate | Microsphere weight | Time of 99% doxorubicin adsorption |
|---|---|---|---|---|
| 1 | 3 | 7.5% DS of about 59% | 300 mg | 20 minutes |
| 2 | 4 | | | 20 minutes |
| 3 | 5 | | | 5 minutes |
| 4 | 5 | 5% DS of 7.5% about 41% | 280 mg | 10 minutes |
| 5 | | | | 5 minutes |
| 6 | 5 | 5% DS of 7.5% about 32% | 280 mg | 20 minutes |
| 7 | | | | 10 minutes |
| 8 | | 10% | 270 mg | 10 minutes |
| 9 | 5 | 7.5% DS of about 20% | 270 mg | 10 minutes |
| 10 | 10 | | | 20 minutes |

Example 5

Degradation Test of Drug-Loaded Hydrogel for Embolization 1 (Degradability Depending on Degree of Substitution)

To investigate the effect of the degree of substitution (DS) of oxidized chondroitin sulfate on the hydrogel degradability, microspheres were manufactured using composition 3 (DS of about 59%), composition 5 (DS of about 41%), and composition 9 (DS of about 20%) in Table 2 by the method in Example 3, respectively, and thermally treated at 150° C. for 2 hours. The manufactured microspheres were weighed to 100 mg each and swollen in 15 ml of 1×PBS, and then the time taken for the microspheres to completely degrade was checked with shaking at 100 rpm in a shaking water bath. The results are shown in Table 4. As shown in Table 4, the time of degradation of microspheres became longer as the degree of substitution of chondroitin sulfate increased.

TABLE 4

| Hydrogel | Composition | Degree of substitution (DS) | Time of thermal treatment | Time of degradation |
|---|---|---|---|---|
| Microsphere 1 | 3 | About 59% | 5 hours | About 30 days |
| Microsphere 2 | 5 | About 41% | 5 hours | About 14 days |
| Microsphere 3 | 9 | About 20% | 5 hours | About 7 days |

Example 6

Degradation Test of Drug-Loaded Hydrogel for Embolization 2 (Degradability Depending on Time of Thermal Treatment)

Figure 3:
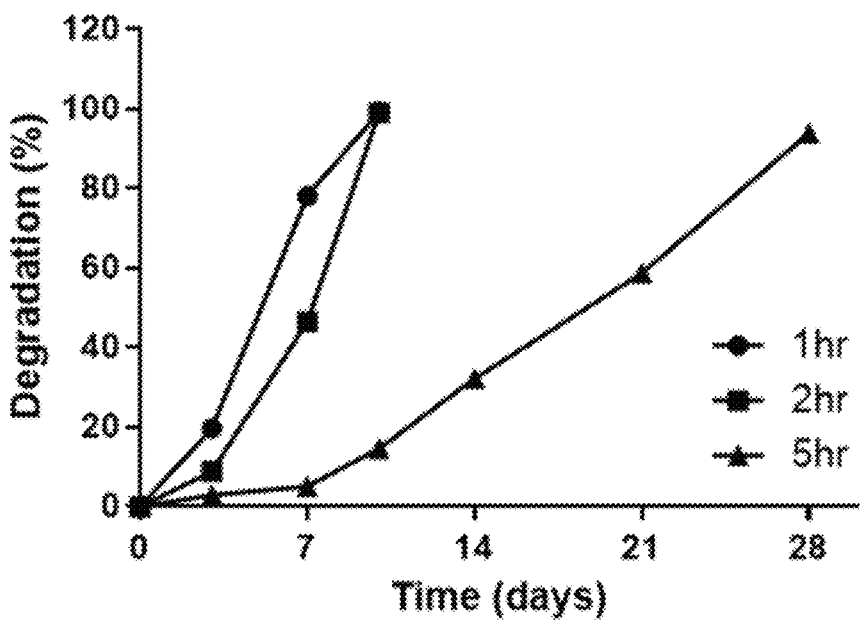
FIG. 3 is a graph showing the degradability of the hydrogel particles of the present disclosure according to the degree of substitution of an anionic polymer.
Figure 4:
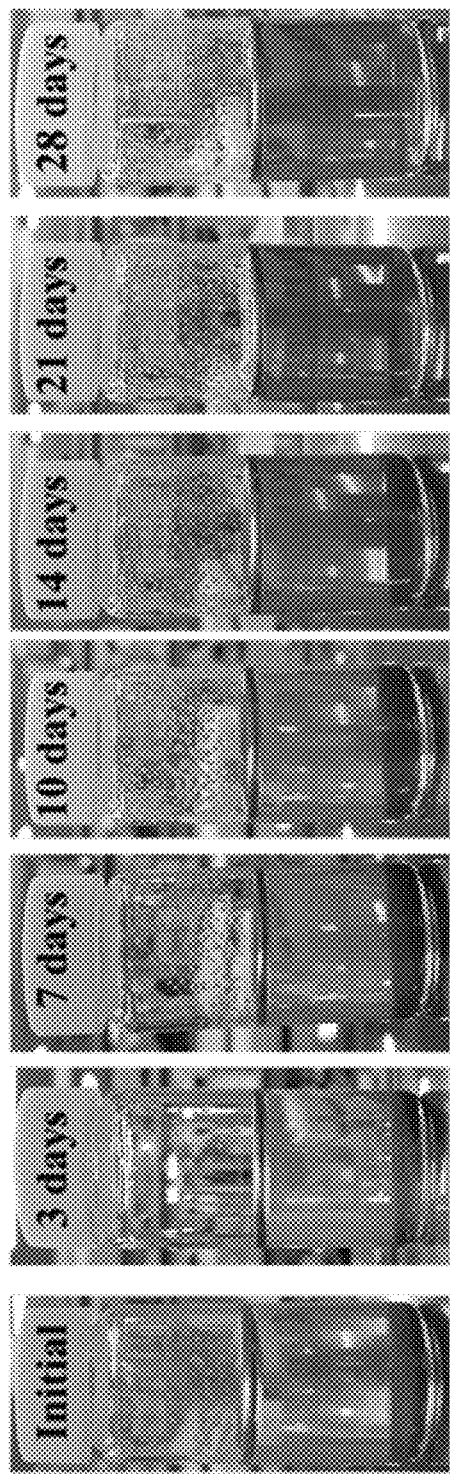
FIG. 4 shows the drug loading ability of the hydrogel particles of the present disclosure according to the presence or absence of thermal curing.

To investigate the effect of the time of thermal treatment on the hydrogel degradability, microspheres were manufactured using composition 7 in Table 2 by the method in Example 3, and thermally treated at 150° C. for 1, 2, and 5 hours, separately. The manufactured microspheres were weighed to 100 mg each and swollen in 15 ml of 1×PBS, and then the time taken for the microspheres to completely degrade was checked with shaking at 100 rpm in a shaking water bath. The results are shown in FIGS. 3 and 4. As shown in FIGS. 3 and 4, the time of degradation became relatively longer as the time of thermal curing increased.

Example 7

Degradation Test of Drug-Loaded Hydrogel for Embolization 3 (Degradability Depending on Content of Gelatin)

To investigate the effect of the content of gelatin on the hydrogel degradability, microspheres were manufactured using ratios of compositions 1, 2, and 3 (gelatin: 3%, 4%, and 5%, respectively, and oxidized chondroitin sulfate: 7.5%) in Table 2 by the method in Example 3, and thermally treated at 150° C. for 5 hours. The manufactured microspheres were weighed to 100 mg each and swollen in 15 ml of 1× PBS, followed by shaking at 100 rpm in a shaking water bath. The remaining microspheres after one month were weighed to calculate the degree of degradation. The results are shown in Table 5. As shown in Table 5, the rate of degradation became faster as the content of gelatin was lower.

TABLE 5

| Hydrogel | Composition | Gelatin content (%) | Time of thermal treatment | Time of degradation |
|---|---|---|---|---|
| Microsphere 4 | 1 | 3 | 5 hours | About 7 days |
| Microsphere 5 | 2 | 4 | 5 hours | About 21 days |
| Microsphere 6 | 3 | 5 | 5 hours | About 30 days |

Example 8

Degradation Test of Drug-Loaded Hydrogel for Embolization 4 (Degradability Depending on Content of Oxidized Chondroitin Sulfate)

To investigate the effect of the content of oxidized chondroitin sulfate on the hydrogel degradability, microspheres were manufactured using ratios of compositions 6, 7, and 8 (gelatin: 5%, and oxidized chondroitin sulfate: 5%, 7.5%, and 10%, respectively) in Table 2 by the method in Example 3, and thermally treated at 150° C. for 5 hours. The manufactured microspheres were weighed to 100 mg each and swollen in 15 ml of 1× PBS, followed by shaking at 100 rpm in a shaking water bath. The remaining microspheres after one month were weighed to calculate the degree of degradation. The results are shown in Table 6. As shown in Table 6, the rate of degradation became faster as the content of oxidized chondroitin sulfate was lower.

TABLE 6

| Hydrogel | Composition | Oxidized chondroitin sulfate (%) | Time of thermal treatment | Time of degradation |
|---|---|---|---|---|
| Microsphere 7 | 6 | 5 | 5 hours | About 4 days |
| Microsphere 8 | 7 | 7.5 | 5 hours | About 7 days |
| Microsphere 9 | 8 | 10 | 5 hours | About 12 days |

Example 9

Figure 5:
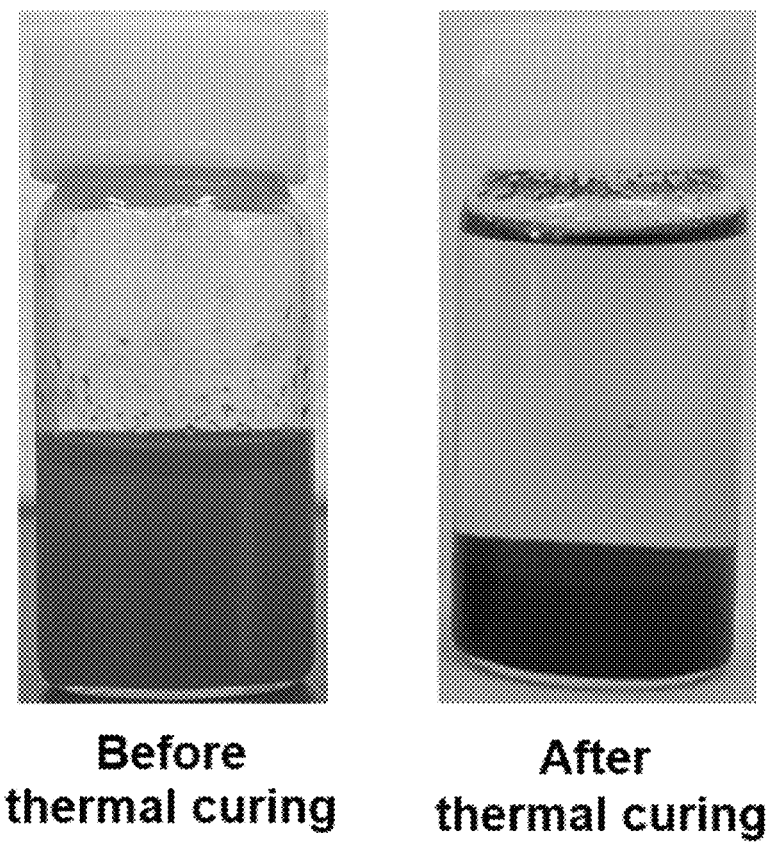
FIG. 5 shows the drug adsorption ability of hydrogel particles manufactured using a non-oxidized anionic polymer, in order to investigate the drug adsorption ability according to the oxidation or non-oxidation of an anionic polymer contained in the hydrogel particles of the present disclosure.

Difference in Drug Loading Ability of Drug-Loaded Hydrogel for Embolization According to Presence or Absence of Thermal Treatment Microspheres were manufactured using the ratio of composition 3 in Table 2 by the method in Example 3. The microspheres having undergone thermal treatment for 2 hours and the microspheres not having undergone thermal treatment were taken at an amount of 280 mg each, and, by the method in Example 4, 10 ml of a 5 mg/ml doxorubicin solution was slowly added to check the degree of doxorubicin adsorption. The naked-eye results after a 30-minute observation are shown in FIG. 5 (Left panel: without thermal treatment, and right panel: with thermal treatment). As shown in the left panel of FIG. 5, in the absence of thermal treatment, little drug adsorption occurred, and the shape of the microparticles was not maintained due to low hardness thereof.

Example 10

Manufacture of Drug-Loaded Hydrogel Particles for Embolization 2 (Sodium Cyanoborohydride Treatment)

After 20 ml of a 5% gelatin solution and 20 ml of a 7.5% oxidized chondroitin sulfate solution were mixed in a tube according to the ratio of composition 3 in Table 2, the tube was immersed in a water bath at 50° C., followed by stirring for 10 minutes. Then, 40 ml of the mixture solution was sprayed into 200 ml of the collection solution n-butyl acetate (10% cellulose acetate butyrate), prepared at 4° C., by using an encapsulator, while the collection solution was stirred, thereby preparing an emulsion (microparticles). Then, 1 g of sodium cyanoborohydride (SCBH) was dissolved in 10 ml of distilled water, and this solution was slowly added to the collection solution containing the microparticles, followed by reaction for 24 hours. After the reaction was completed, the stirring was stopped, the particles formed in the collection solution were settled by a long period of stabilization, and the collection solution in the upper layer was discarded. Washing was sequentially conducted using n-butyl acetate and acetone. The microparticles were completely swollen in distilled water, and sodium cyanoborohydride remaining in the microparticles was removed by carrying out stirring for 30 minutes and exchanging of distilled water three times, and then hydrogel particles with a diameter of 100-300 μm were collected through sieving. The collected hydrogel particles were dehydrated with acetone, followed by vacuum drying, thereby obtaining final microspheres.

Example 11

Manufacture of Drug-Loaded Hydrogel Particles for Embolization 3 (Glutaraldehyde Treatment)

After 20 ml of a 5% gelatin solution and 20 ml of a 7.5% oxidized chondroitin sulfate solution were mixed in a tube according to the ratio of composition 3 in Table 2, the tube was immersed in a water bath at 50° C., followed by stirring for 10 minutes. Then, 40 ml of the mixture solution was sprayed into 200 ml of the collection solution n-butyl acetate (10% cellulose acetate butyrate), prepared at 4° C., by using an encapsulator, while the collection solution was stirred, thereby preparing an emulsion (microparticles). Then, 10 ml of 25% glutaraldehyde (GA) was slowly added to the collection solution containing the microparticles, followed by reaction for 24 hours. After the reaction was completed, the stirring was stopped, and the particles were settled by a long period of stabilization, the collection solution in the upper layer was discarded. Washing was sequentially conducted using n-butyl acetate and acetone. The microparticles were completely swollen in distilled water, and glutaraldehyde remaining in the microparticles was removed by carrying out stirring for 30 minutes and exchanging of distilled water three times, and then hydrogel particles with a diameter of 100-300 μm were collected through sieving. The collected hydrogel particles were dehydrated with acetone, followed by vacuum drying, thereby obtaining final microspheres.

Example 12

Manufacture of Drug-Loaded Hydrogel Particles for Embolization 4 (EDC/NHS Treatment)

After 20 ml of a 5% gelatin solution and 20 ml of a 7.5% chondroitin sulfate solution were mixed in a tube according to the ratio of composition 3 in Table 2, the tube was immersed in a water bath at 50° C., followed by stirring for 10 minutes. Then, 40 ml of the mixture solution was sprayed into 400 ml of the collection solution n-butyl acetate (10% cellulose acetate butyrate), prepared at 4° C., by using an encapsulator, while the collection solution was stirred, thereby preparing an emulsion (microparticles). Then, 1 g of N-(3-dimethylaminopropyl)-N'-ethylcarbodiimide hydrochloride (EDC) and 1 g of N-hydroxysuccinimide (NHS) were dissolved in 10 ml of distilled water, and this solution was slowly added to the collection solution containing the microparticles, followed by reaction for 24 hours. After the reaction was completed over, the stirring was stopped, the particles were settled by a long period of stabilization, and the collection solution in the upper layer was discarded. Washing was sequentially conducted using n-butyl acetate and acetone. The microparticles were completely swollen in distilled water, and EDC/NHS remaining in the microparticles was removed by carrying out stirring for 30 minutes each and exchanging of distilled water three times, and then hydrogel particles with a diameter of 100-300 μm were collected through sieving. The collected hydrogel particles were dehydrated with acetone, followed by vacuum drying, thereby obtaining final microspheres.

Example 13

Difference in Ability of Drug-Loaded Hydrogel Particles for Embolization According to Manufacturing Method (Drug Adsorption Time and Degradability)

In order to investigate the difference in drug loading ability according to the manufacturing method, a doxorubicin adsorption test was performed, by the method in Example 4, on a total of four types of microspheres, that is, hydrogel particles manufactured through thermal treatment in Example 3, hydrogel particles manufactured by addition of sodium cyanoborohydride in Example 10, hydrogel particles manufactured by addition of glutaraldehyde in Example 11, and hydrogel particles manufactured by addition of EDC/NHS in Example 12. In addition, hydrogel particles without doxorubicin adsorption were weighed to 100 mg each and placed in 15 ml of 1×PBS, and the degradability was checked for three months with shaking at 100 rpm in a shaking water bath. The results are shown in Table 7. As shown in Table 7, the drug adsorption ability of the hydrogel particles manufactured using SCBH, GA, or EDC/NHS was significantly lower than that of the hydrogel particles manufactured by thermal curing. The hydrogel particles manufactured by thermal curing can control the time of degradation thereof by the degree of substitution (DS) of chondroitin sulfate (CS) but showed no great difference in drug adsorption ability. However, the microspheres manufactured using SCBH, GA, or EDC/NHS can control the time of degradation thereof according to the amount of SCBH, GA, or EDC/NHS used and also showed a significant difference in drug adsorption ability.

Example 14

Manufacture of Drug-Loaded Hydrogel Particles for Embolization 5 (Non-Oxidized Chondroitin Sulfate vs. Oxidized Chondroitin Sulfate)

Figure 6:
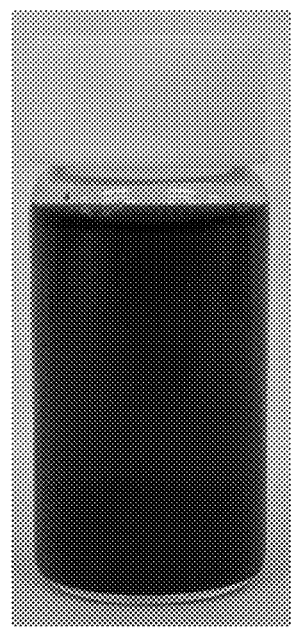
FIG. 6 shows the drug release ability of DC Bead and HepaSphere, existing commercially available products, in order to investigate the drug release ability of the hydrogel particles of the present disclosure.

In order to investigate the effect of the oxidation of chondroitin sulfate on drug-adsorption of hydrogel, hydrogel particles were manufactured by the same method as in Example 3 except that non-oxidized chondroitin sulfate was used instead of oxidized chondroitin sulfate. Then, the drug adsorption ability of the manufactured hydrogel particles was checked by the method in Example 4. The results are shown in FIG. 6. As shown in FIG. 6, favorable doxorubicin adsorption did not occur in the hydrogel particles manufactured of non-oxidized chondroitin sulfate. The reason seems to be that chondroitin sulfate, when not oxidized, cannot conjugate to gelatin, and thus non-oxidized chondroitin sulfate was all washed off and removed during the manufacture of microspheres. Therefore, it could be seen that hydrogel particles manufactured of non-oxidized chondroitin sulfate showed a very poor drug adsorption ability.

Example 15

Figure 7:
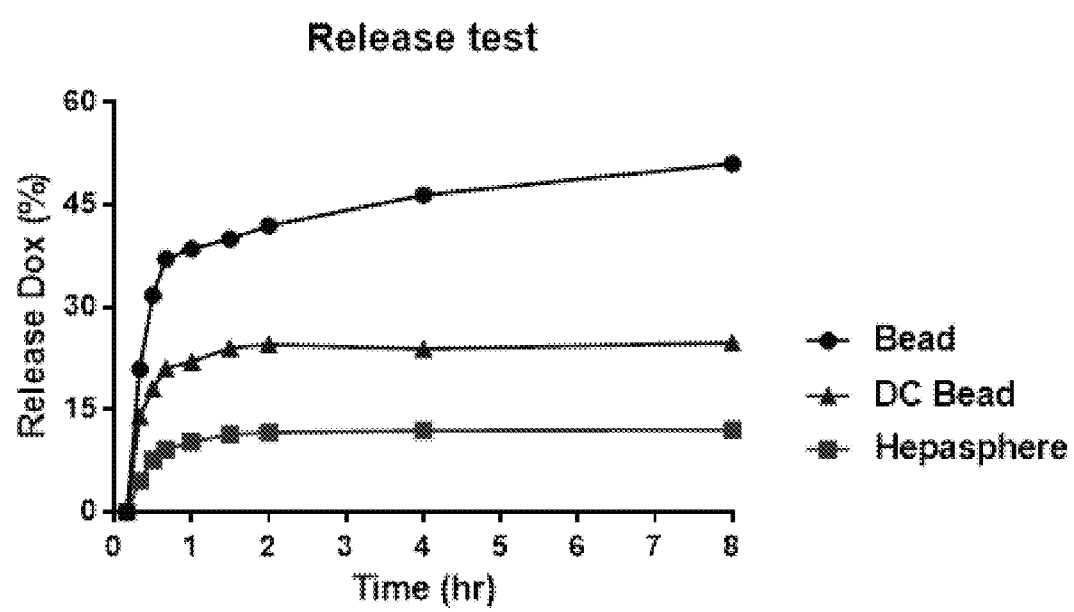
FIG. 7 shows an image of hydrogel particles manufactured of collagen and oxidized chondroitin sulfate of the present disclosure and an image of hydrogel particles after loading doxorubicin.

Drug Release Comparison Test of Drug-Loaded Hydrogel for Embolization of Present Disclosure and Commercially Available Drug-Loaded Embolic Agents After 50 mg of doxorubicin was adsorbed onto the microspheres 2 (100-300 μm) in Example 5 and the commercially available embolic agents HepaSphere™ (200-400 μm) and DC Bead™ (100-300 μm), a release test was conducted in 1×PBS solution at 50 rpm. As shown in the results of FIG. 7, HepaSphere™ and DC Bead™ hardly release the drug after 2 hours, but the hydrogel (microsphere 2, Bead) presented in the present disclosure continuously released the drug. In addition, microsphere 2 (Bead) completely degraded over one month to release the overall drug, showing a final drug release rate of 100%, but the non-degradable HepaSphere™ and DC Bead™ showed a final drug release rate of less than 30%, indicating a very great difference in drug release rate.

Example 16

Manufacture of Drug-Loaded Hydrogel Particles for Embolization 6 (Collagen and Oxidized Chondroitin Sulfate Particles)

After 20 ml of a 10% gelatin solution and 20 ml of a 7.5% oxidized chondroitin sulfate solution were mixed, the mix-

TABLE 7

| Hydrogel | Microspheres | Crosslinking method | | Time of 99% doxorubicin adsorbed | Degree of 100% degradation |
|---|---|---|---|---|---|
| Microsphere 10 | 300 mg | Thermal curing | CS (DS59%) | about 5 minutes | about 12 weeks |
| Microsphere 11 | | | CS (DS41%) | about 5 minutes | about 10 weeks |
| Microsphere 12 | 300 mg | Sodium cyanoboro | 1 g | about 30 minutes | 13 weeks or more |
| Microsphere 13 | | hydride (SCBH) | 0.5 g | about 60 minutes | about 8 weeks |
| Microsphere 14 | 300 mg | Glutaraldehyde (GA) | 10 ml | 40 minutes or more | 13 weeks or more |
| Microsphere 15 | | | 5 ml | 60 minutes or more | about 10 weeks |
| Microsphere 16 | 300 mg | EDC/NHS | 1 g/1 g | about 40 minutes | 13 weeks or more |
| Microsphere 17 | | | 0.5 g/0.5 g | 60 minutes or more | about 8 weeks |

Figure 8:
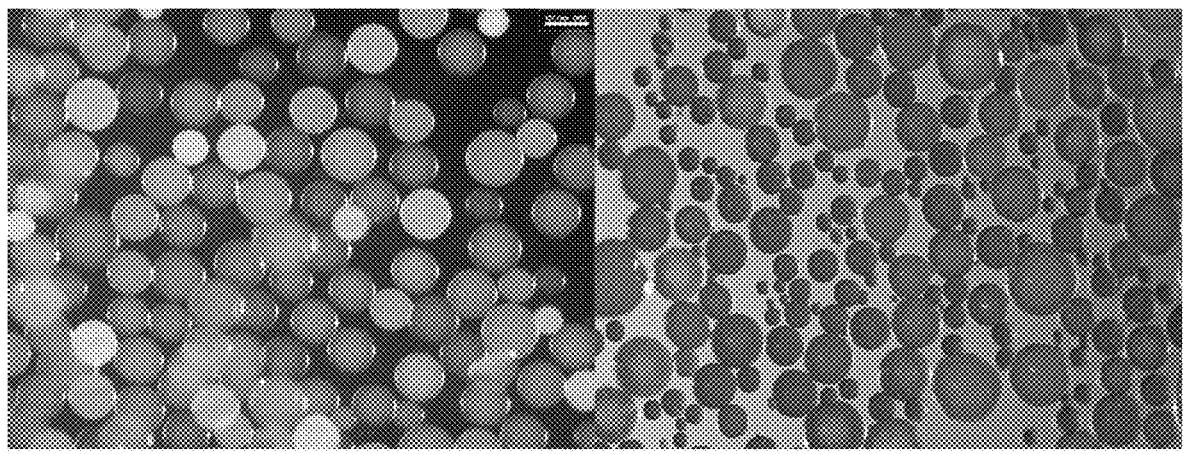
FIG. 8 shows an image of hydrogel particles manufactured of gelatin and oxidized dextran sulfate of the present disclosure and an image of hydrogel particles after loading doxorubicin.

* Observed once a week ture was stirred for 10 minutes. Then, the mixture solution was sprayed into 200 ml of the collection solution n-butyl acetate (10% cellulose acetate butyrate), prepared at 4° C., by using an encapsulator, while the collection solution was stirred, thereby preparing an emulsion (microparticles). After the spraying was completed, the stirring was stopped, the particles were settled by a long period of stabilization, and the collection solution in the upper layer was discarded. Washing was sequentially conducted using n-butyl acetate and acetone, and followed by vacuum drying, thereby obtaining microparticles. The obtained microparticles were subjected to thermal treatment at 150° C. for 2 hours, and then completely swollen in distilled water, and hydrogel particles with a diameter of 100-300 μm were collected through sieving. The collected hydrogel particles were dehydrated with acetone, followed by vacuum drying, thereby obtaining final powdered microspheres. The images of the hydrogel particles when the manufactured powdered microspheres were swollen in distilled water and when doxorubicin was loaded are shown in FIG. 8.

Example 17

Manufacture of Drug-Loaded Hydrogel Particles for Embolization 8 (Gelatin and Oxidized Dextran Sulfate Particles)

After 20 ml of a 5% gelatin solution and 20 ml of a 7.5% oxidized dextran sulfate (DS 20%) were mixed using the ratio of composition 3 in Table 2, the mixture was stirred for 10 minutes. Then, the mixture solution was sprayed into 200 ml of the collection solution n-butyl acetate (10% cellulose acetate butyrate) at 4° C. by using an encapsulator while the collection solution was stirred, thereby preparing an emulsion (microparticles). After the spraying was completed, the stirring was stopped, the particles were settled by a long period of stabilization, and the collection solution in the upper layer was discarded. Washing was conducted using n-butyl acetate and acetone, and followed by vacuum drying, thereby obtaining microparticles. The obtained microparticles were subjected to thermal treatment at 150° C. for 2 hours, and completely swollen in distilled water, and hydrogel particles with a diameter of 100-300 μm were collected through sieving. The collected hydrogel particles were dehydrated with acetone, followed by vacuum drying, thereby obtaining final powdered microspheres. The images of the hydrogel particles when the manufactured powdered microspheres were swollen in distilled water and when doxorubicin was loaded are shown in FIG. 9.

What is claimed is:

1. A method for manufacturing microparticles, the method comprising:
    (a) dissolving gelatin, collagen, or a mixture thereof in an aqueous solvent;
    (b) dissolving oxidized chondroitin sulfate in an aqueous solvent forming a biodegradable anionic polymer solution; and
    (c) mixing the solution of gelatin, collagen, or the mixture thereof and the biodegradable anionic polymer solution;
    (d) adding the mixture solution as the resultant product in step
    (c) to an organic solvent, followed by emulsification through stirring;
    (e) washing and drying the microparticles generated by the emulsification; and
    (f) subjecting the microparticles generated by the emulsification to thermal treatment at a temperature of 90 to 200° C. for 0.5 to 5 hours.

2. The method of claim 1, wherein step b) further comprises dissolving one or more polymers selected from the group consisting of oxidized dextran sulfate, oxidized dermatan sulfate, oxidized sodium alginate sulfate, oxidized heparin, oxidized keratan sulfate, oxidized hyaluronic acid, and a mixture thereof.

3. The method of claim 1, wherein the organic solvent is n-butyl acetate, cellulose acetate butyrate, medium chain triglyceride (MCT) oil, or a mixture solvent thereof.

4. The method of claim 1, wherein the washing is conducted with an organic solvent selected from n-butyl acetate, cellulose acetate butyrate, medium chain triglyceride (MCT) oil, or a mixture solvent thereof.

5. The method of claim 1, further comprising (g) washing the thermally treated microparticles.

6. The method of claim 5, further comprising (h) dehydrating and drying the microparticles.

* * * * *